(12) United States Patent
Shimada et al.

(10) Patent No.: US 10,420,681 B2
(45) Date of Patent: Sep. 24, 2019

(54) DEVICE AND METHOD FOR CARRYING SHEET MATERIAL OF WORN ARTICLE

(71) Applicant: ZUIKO CORPORATION, Osaka (JP)

(72) Inventors: Takahiro Shimada, Osaka (JP); Susumu Honge, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 282 days.

(21) Appl. No.: 15/524,086

(22) PCT Filed: Nov. 6, 2015

(86) PCT No.: PCT/JP2015/081318
§ 371 (c)(1),
(2) Date: May 3, 2017

(87) PCT Pub. No.: WO2016/076223
PCT Pub. Date: May 19, 2016

(65) Prior Publication Data
US 2017/0348159 A1    Dec. 7, 2017

(30) Foreign Application Priority Data

Nov. 14, 2014    (JP) .................................. 2014-231569

(51) Int. Cl.
*B65H 20/10*    (2006.01)
*A61F 13/15*    (2006.01)
(Continued)

(52) U.S. Cl.
CPC .. *A61F 13/15764* (2013.01); *A61F 13/15707* (2013.01); *A61F 13/15739* (2013.01);
(Continued)

(58) Field of Classification Search
CPC ............................ B65H 20/10; B65H 2801/37
(Continued)

(56) References Cited

U.S. PATENT DOCUMENTS 7,533,709 B2 * 5/2009 Meyer .............. A61F 13/15699
156/516
2002/0129888 A1    9/2002 Otsubo et al.
(Continued)

FOREIGN PATENT DOCUMENTS

JP    2002-272781 A    9/2002
JP    2010-035932 A    2/2010
(Continued)

OTHER PUBLICATIONS

International Search Report Issued in PCT/JP2015/081318 dated Jan. 26, 2016.

*Primary Examiner* — Scott W Dodds
(74) *Attorney, Agent, or Firm* — Renner, Otto, Boisselle & Sklar, LLP

(57) ABSTRACT

A carrying device includes: a carrying section having a receiving surface to be in contact with a first sheet material that is continuous in a carrying direction, wherein one edge of the first sheet material is wave-shaped, the carrying section defining an inclined slit portion, wherein the inclined slit portion defines an opening on the receiving surface, wherein the inclined slit portion extends in an inclined direction so as to be displaced from a proximal side toward a distal side of a protruding portion while extending downstream in the direction of carrying the first sheet material, and wherein the inclined slit portion sucks the protruding portion along the wave-shaped edge; and a box defining a suction space that keeps the inclined slit portion under a negative pressure so that the protruding portion is pulled into the inclined slit portion by suction.

5 Claims, 12 Drawing Sheets

(51) Int. Cl.
  *B65H 20/12* (2006.01)
  *A61F 13/00* (2006.01)
(52) U.S. Cl.
  CPC ........ *B65H 20/12* (2013.01); *A61F 13/15601* (2013.01); *A61F 2013/15715* (2013.01); *B65H 2801/57* (2013.01)
(58) Field of Classification Search
  USPC .............................................. 242/615, 615.1
  See application file for complete search history.

(56) References Cited

U.S. PATENT DOCUMENTS

| | | |
|---|---|---|
| 2006/0254708 A1 | 11/2006 | Wada et al. |
| 2010/0032263 A1 | 2/2010 | Yamamoto |
| 2011/0049209 A1 | 3/2011 | Yamamoto |
| 2012/0224012 A1* | 9/2012 | Inoue ...................... B41F 21/00 347/104 |
| 2013/0244855 A1 | 9/2013 | Shinohara |

FOREIGN PATENT DOCUMENTS

| | | |
|---|---|---|
| JP | 2010-228913 A | 10/2010 |
| JP | 2012-075589 A | 4/2012 |
| WO | 2005-013871 A1 | 2/2005 |

* cited by examiner

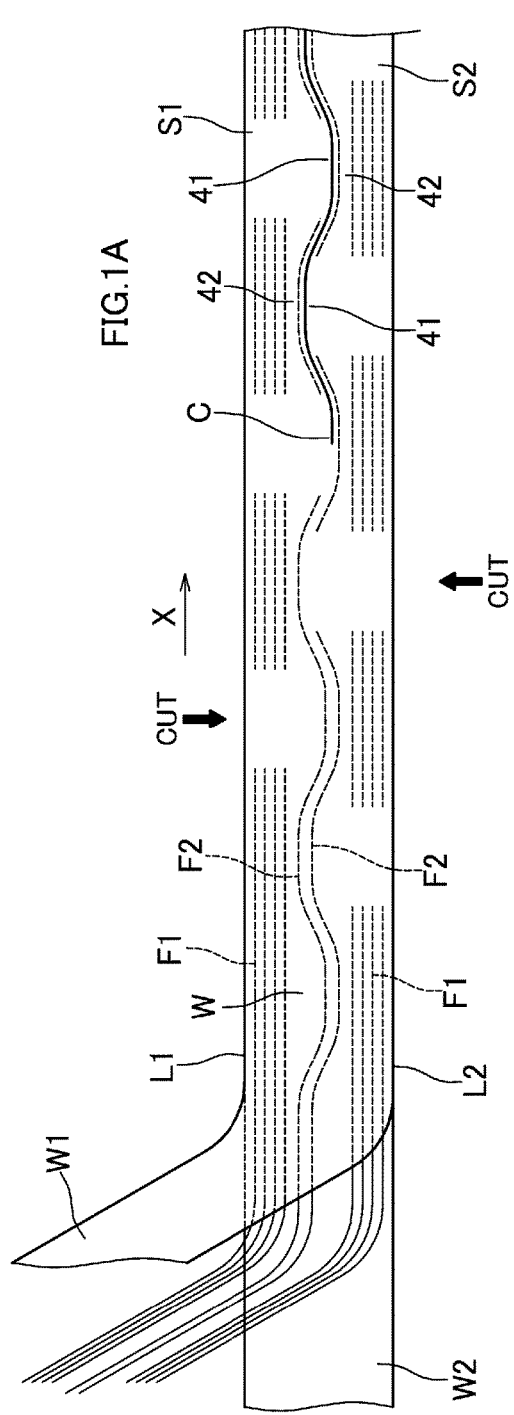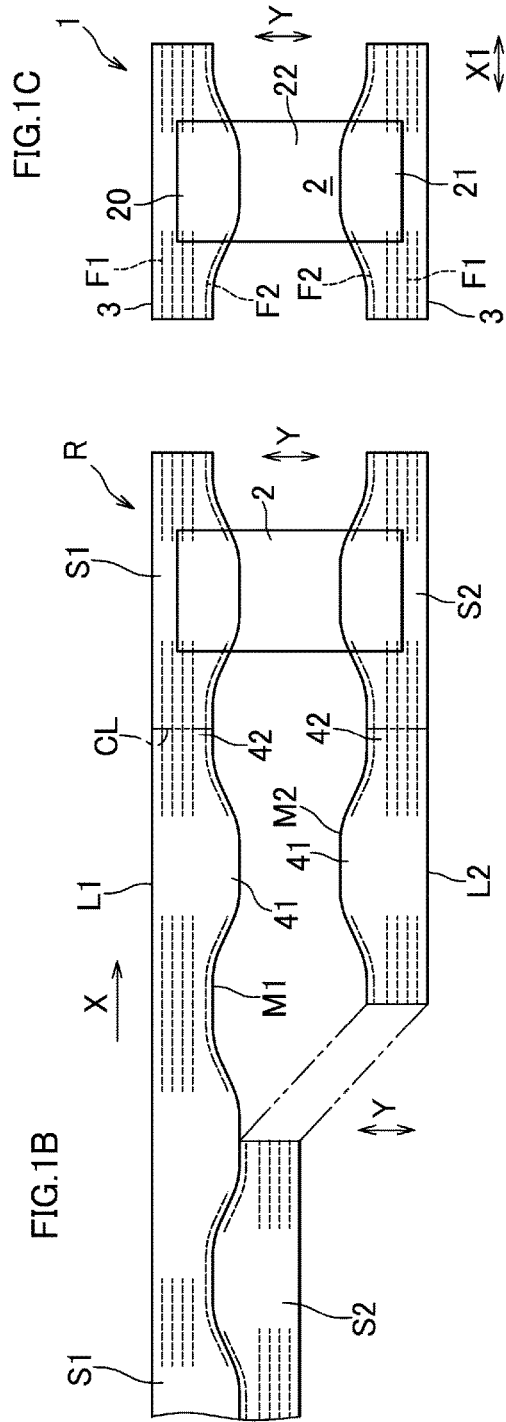

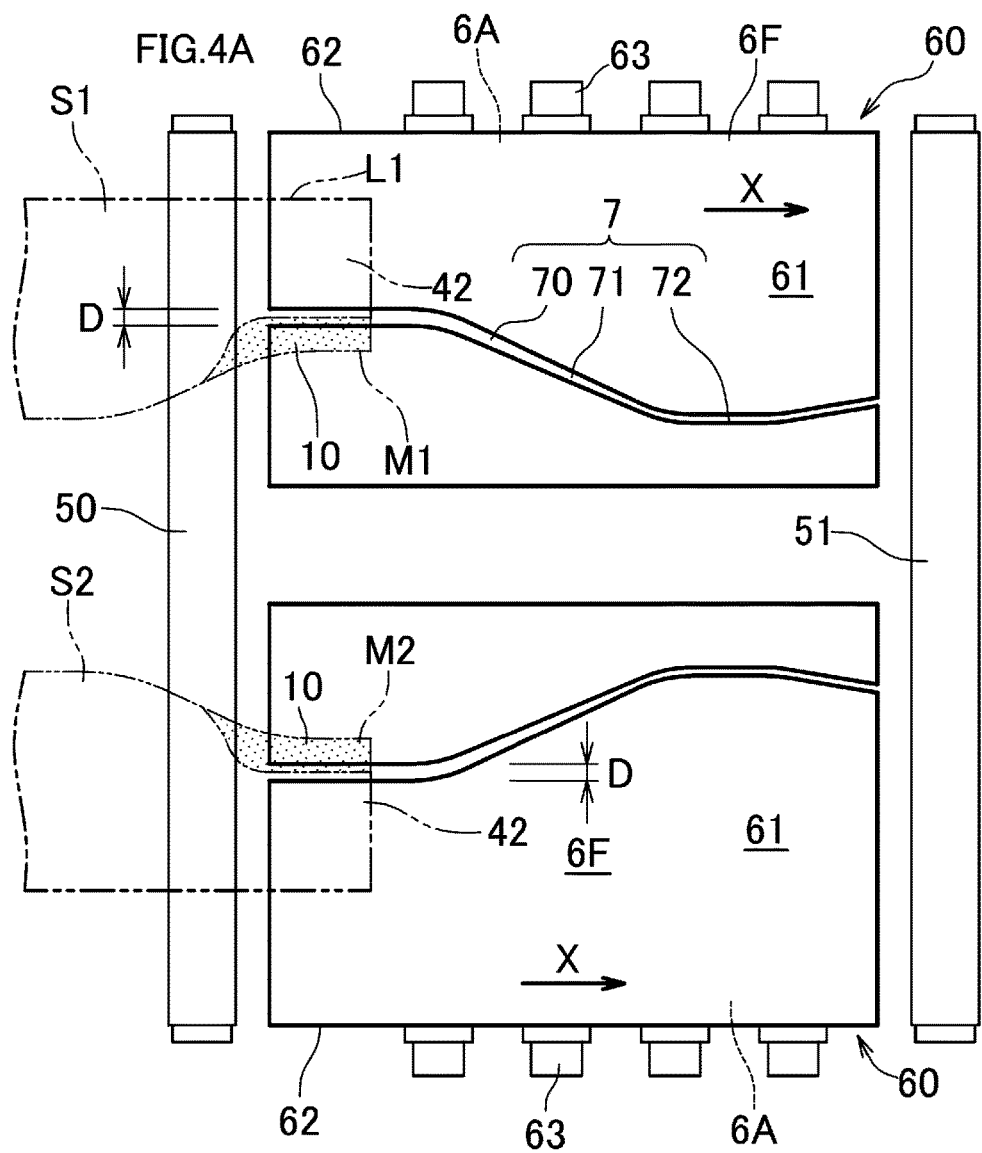
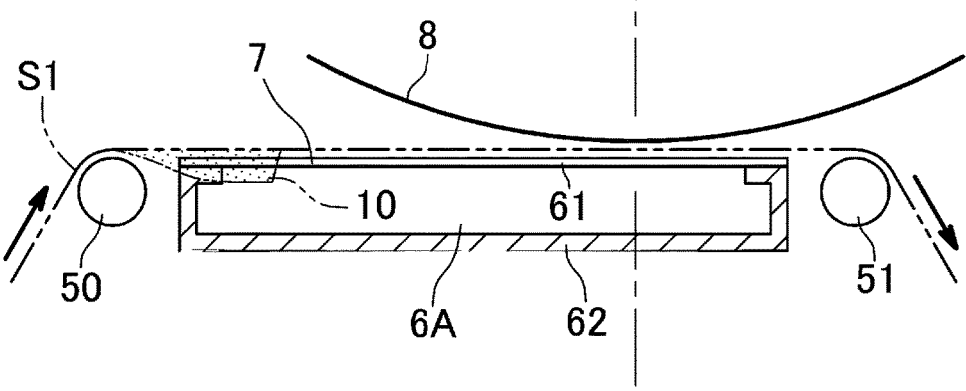

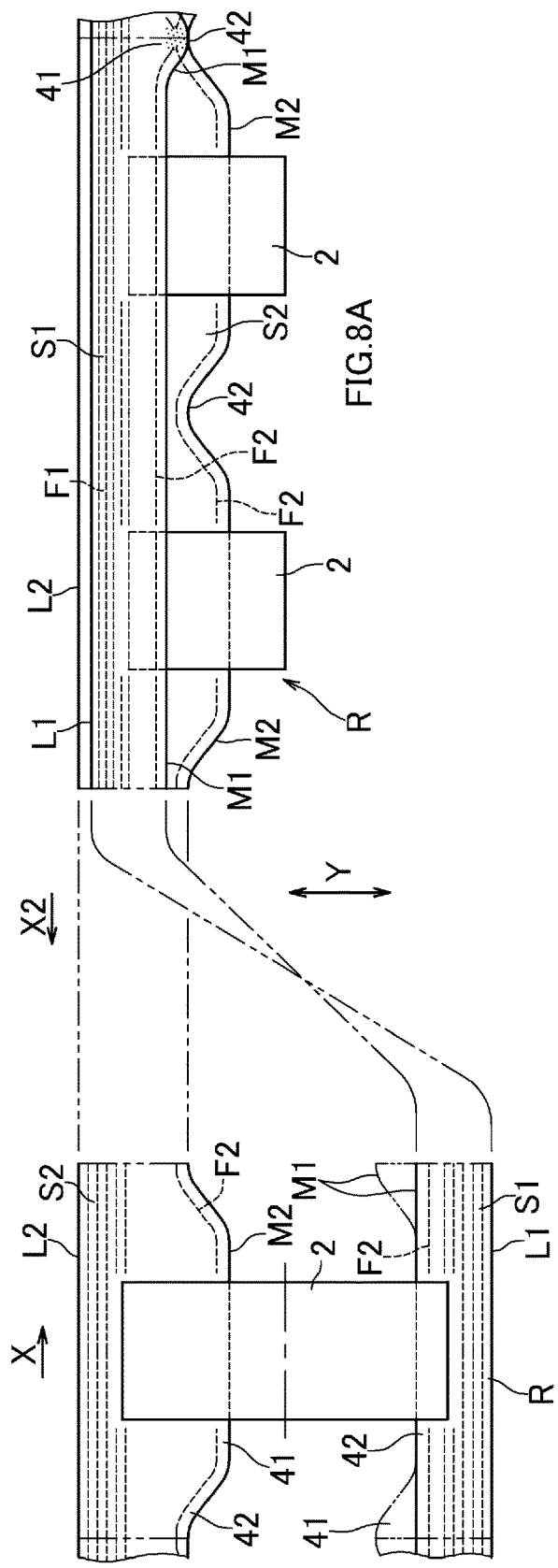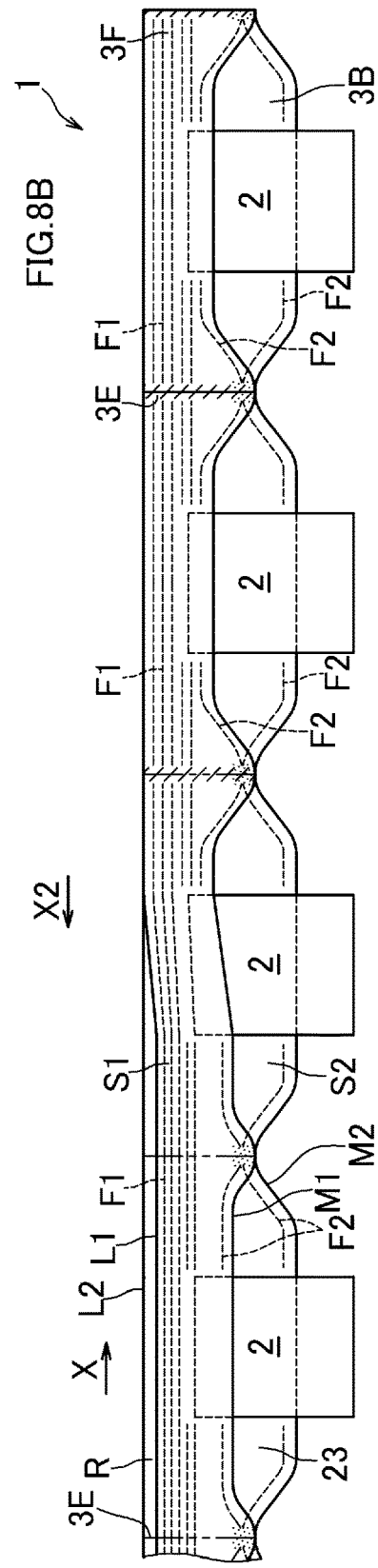

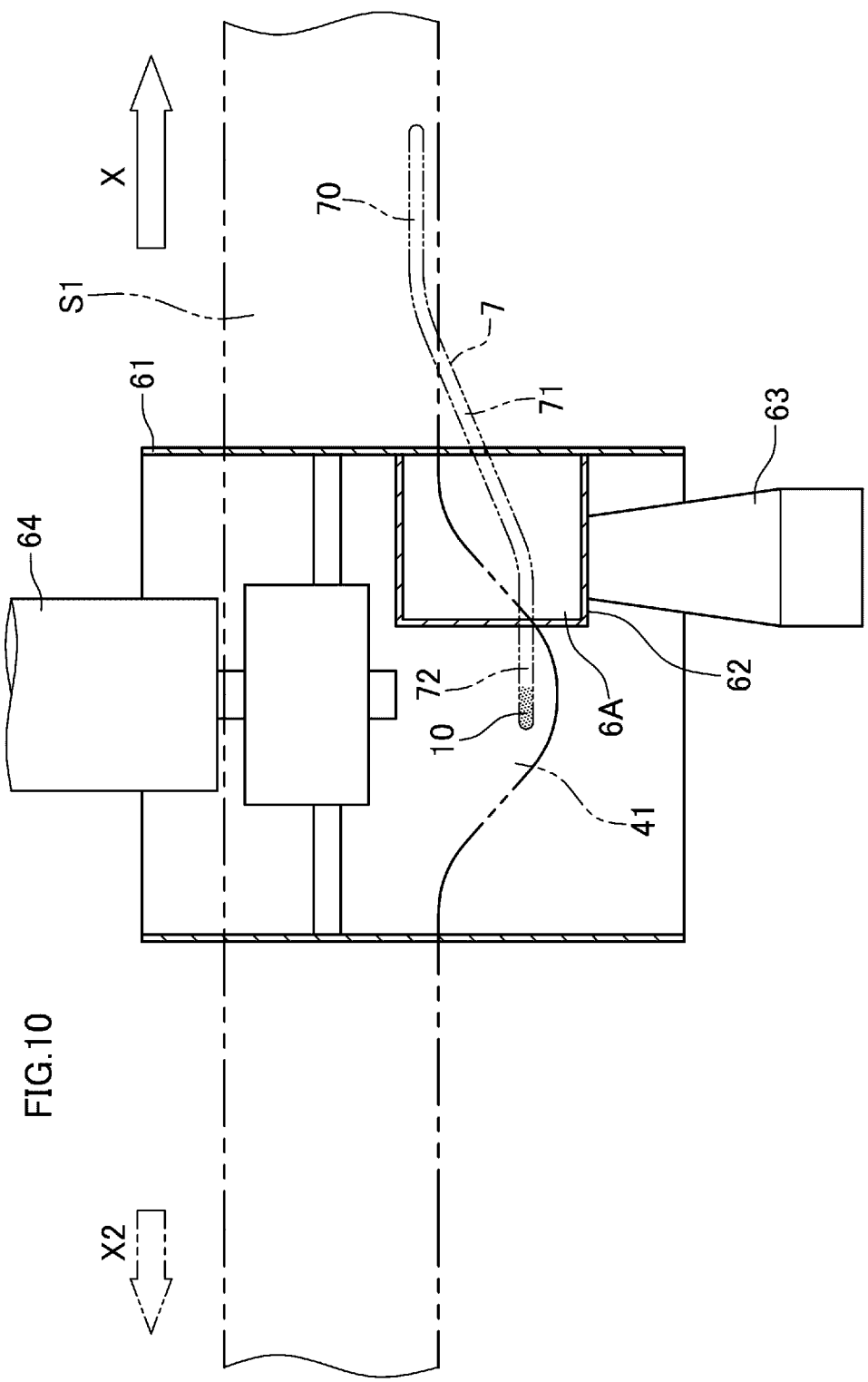

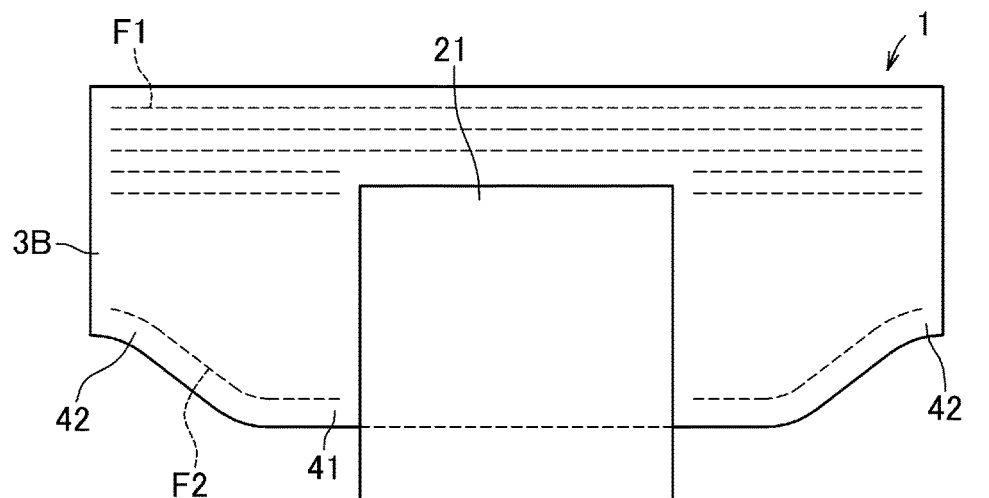
FIG.12A
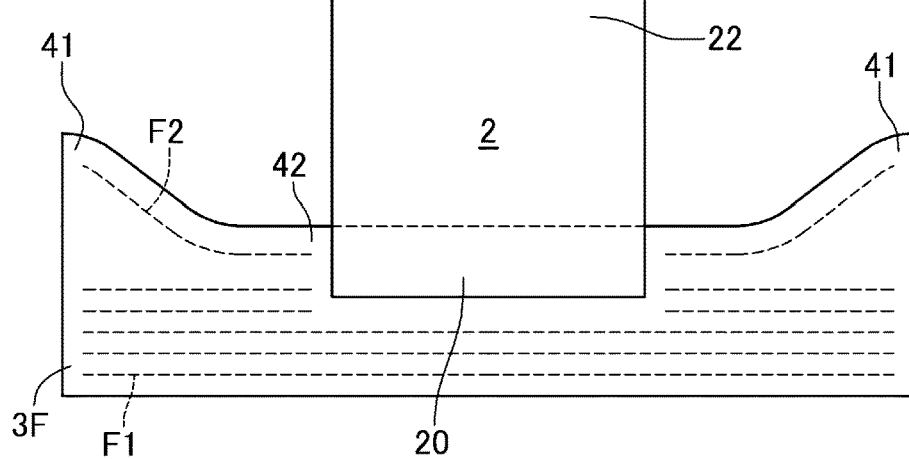
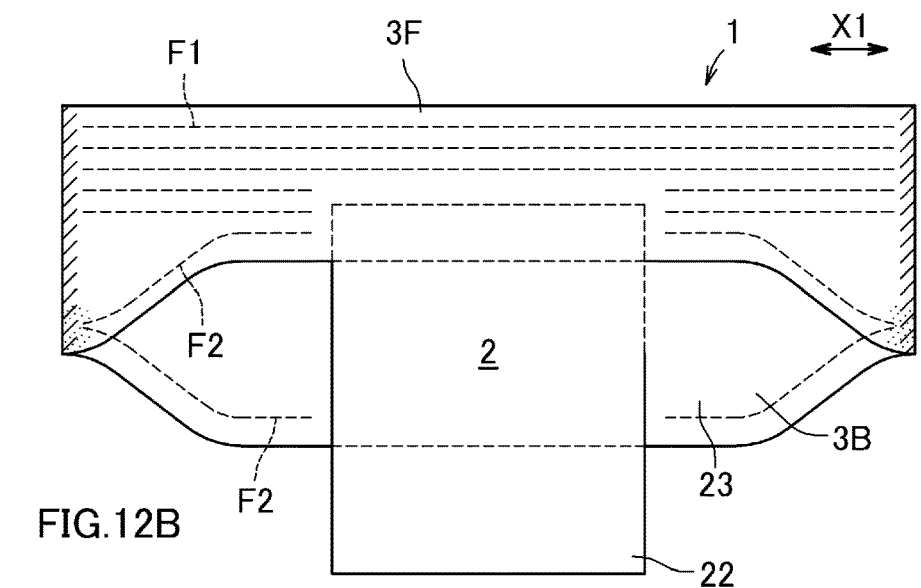
FIG.12B

DEVICE AND METHOD FOR CARRYING SHEET MATERIAL OF WORN ARTICLE

TECHNICAL FIELD

The present invention relates to a device and a method for carrying a sheet material of a worn article, and relates to a device and a method for carrying a web of a disposable worn article, such as a disposable diaper or a disposable mask, for example, during the manufacture of the article.

BACKGROUND ART

It is well known in the art that in the process of manufacturing disposable diapers, or the like, a continuous web is slit into two or three pieces along a wave-shaped severing line extending in the carrying direction.

CITATION LIST

Patent Literature

[First Patent Document] JP2002-272781A (Abstract)
[Second Patent Document] WO2005/013871A1 (Abstract)

SUMMARY OF INVENTION

However, divided webs obtained by slitting in a wave-shaped pattern have periodic protruding portions that protrude in the width direction perpendicular to the carrying direction. It is difficult to have these protruding portions under a tension in the carrying direction. Therefore, the shape of the protruding portions is likely to be unstable while being carried. Particularly, when an elastic member is placed extending along the edge of the protruding portion, the protruding portion is likely to be creased by the shrinking force of the elastic member.

It is therefore an object of the present invention to provide a device and a method for carrying a sheet material of a worn article, with which the shape of a sheet material having periodic protruding portions is likely to be stable while the sheet material is carried.

A device of the present invention includes:

a carrying section having a contact surface to be in contact with one surface of a first sheet material that is continuous in a carrying direction, wherein at least one edge of the first sheet material is wave-shaped so as to repeatedly define protruding portions and depressed portions, the carrying section defining an inclined slit portion, wherein the inclined slit portion defines an opening on the contact surface, wherein the inclined slit portion extends in an inclined direction so as to be displaced from a proximal side toward a distal side of the protruding portion while extending in a relative direction in which the first sheet material moves (displaces, travels) relative to the contact surface, and wherein the inclined slit portion sucks at least a portion of the protruding portion along the wave-shaped edge; and a box defining a suction space that is continuous with the inclined slit portion and keeps the inclined slit portion under a negative pressure so as to suck the protruding portion of the first sheet material so that the at least a portion of the protruding portion is pulled into the inclined slit portion.

A method of the present invention using the device of the present invention includes the steps of:

continuously carrying the first sheet material while keeping the first sheet material under a tension in a carrying direction of the first sheet material;

sucking the wave-shaped edge into the inclined slit portion while carrying the first sheet material; and allowing a part or whole of the sucked edge to emerge onto the contact surface of the carrying section from the inclined slit portion as the first sheet material is carried, thereby stretching (drawing) the protruding portion in a width direction perpendicular to the carrying direction.

According to the present invention, the protruding portion, which has been sucked into the inclined slit portion, emerges onto the contact surface from the inclined slit portion as the sheet material is carried. Then, the protruding portion is kept under a tension in the width direction, thereby stretching the protruding portion in the width direction and stabilizing the shape of the protruding portion. For example, if the protruding portion is creased in the width direction before the protruding portion is sucked into the inclined slit portion, the creases will be reduced or straightened (smoothed) by the stretching.

In the present invention, the term "wave-shaped (pattern)" encompasses cases where the edge has a rectangular wave shape, as well as cases where the edge is a smooth curve such as a sinusoidal curve or a trapezoidal curve that is approximate to such a curve.

The "carrying section" is preferably a plate having a smooth surface such as a metal plate or a resin plate, but it may be a metal or resin ingot, or a combination of such a plate or an ingot with a conveyor belt. If the "carrying section" is formed by a plate, the plate may be a flat plate or a curved plate, or may be a cylinder-shaped drum.

Note that the carrying section may or may not have a driving force.

As used herein, the "relative direction" refers to the direction of the velocity (vector) of the first sheet material with respect to the contact surface. For example, if the first sheet material is carried while the contact surface is standing still, the relative direction is the carrying direction of the first sheet material. On the other hand, if the contact surface and the first sheet material are both moving in the first direction, and the velocity of the contact surface is greater than that of the first sheet material, the relative direction is opposite to the carrying direction of the first sheet material. If the contact surface and the first sheet material are moving in opposite directions, the relative direction is the carrying direction of the first sheet material.

Note that if the carrying section is a flat plate or a curved plate, the carrying section typically does not move. If the carrying section is a drum, the carrying section typically rotates in the circumferential direction of the drum.

There is no particular limitation on the "box" as long as the suction space can be defined therein, and the suction space may be defined by the box by itself, or by the box in cooperation with the carrying section such as the plate.

The box preferably has a rectangular parallelepiped shape or a dome shape, of which the volume is significantly greater as compared with the width of the inclined slit portion in order to stabilize the magnitude of the negative pressure, but there is no particular limitation on the shape and size of the box in the present invention. For example, the box may be an elongated box or a manifold formed by a pipe extending along the inclined slit.

BRIEF DESCRIPTION OF DRAWINGS

FIG. 1A, FIG. 1B and FIG. 1C are conceptual diagrams each showing a method for manufacturing a worn article according to an embodiment of the present invention.

FIG. 4A and FIG. 4B are a schematic plan view and side view, respectively, showing the carrying device.

FIG. 8A and FIG. 8B are conceptual diagrams each showing a method for manufacturing a worn article according to another embodiment of the present invention.

FIG. 10 is a schematic cross-sectional view showing the carrying device.

FIG. 12A and FIG. 12B are a developed view and a plan view, respectively, showing the worn article.

DESCRIPTION OF EMBODIMENTS

Figure 2:
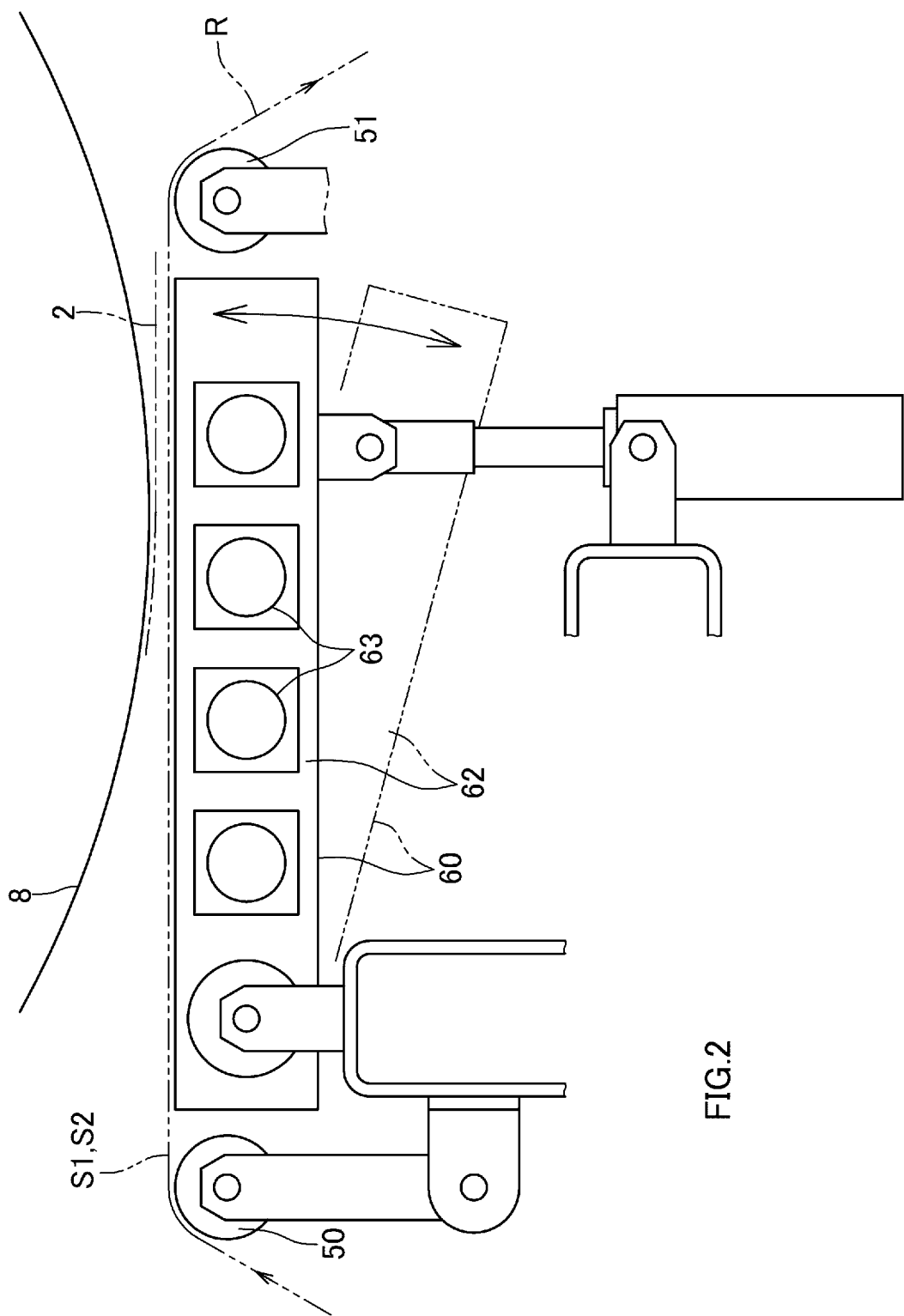
FIG. 2 is a schematic side view showing one embodiment of a carrying device.

Preferably, in the device of the present invention, the carrying section defines an upstream slit portion that is continuous with an upstream end of the inclined slit portion in the relative direction, and a downstream slit portion that is continuous with a downstream end of the inclined slit portion in the relative direction.

In this case, the upstream slit portion is preferably formed so that the inclined slit portion smoothly sucks the protruding portion of the edge. For example, the upstream slit portion preferably extends to the upstream end of the inclined slit portion, in parallel to the carrying direction, or with a smaller inclination than an inclination of the inclined slit portion. Note that the upstream slit portion may have an opposite inclination to an inclination of the inclined slit portion.

Preferably, the downstream slit portion is formed so that the protruding portion, which has been pulled into the inclined slit portion, emerges smoothly onto the contact surface from the inclined slit portion and so that the protruding portion, which has emerged onto the contact surface, will not be creased again.

For example, the downstream slit portion may extend in parallel to the carrying direction from the downstream end of the inclined slit portion or may extend in the carrying direction from the downstream end of the inclined slit portion with a smaller inclination than an inclination of the inclined slit portion.

Alternatively, the downstream slit portion may extend from the downstream end of the inclined slit portion with an opposite inclination to an inclination of the inclined slit portion. The downstream slit portion may extend slightly from the downstream end of the inclined slit portion in parallel to the carrying direction, and further extend in an inclined direction with respect to the carrying direction with an inclination that is smaller than, and opposite to, an inclination of the inclined slit portion.

If the downstream slit portion includes a section where the inclination is opposite to that of the inclined slit portion, the protruding portion is drawn toward the downstream slit portion and the creases of the protruding portion are likely to be kept straightened even after the edge having a trapezoidal curve or sinusoidal curve shape emerges onto the contact surface.

Preferably, the upstream slit portion and/or the inclined slit portion has a width that decreases as the upstream slit portion and/or the inclined slit portion extends from an upstream side to a downstream side in the carrying direction.

In this case, an upstream portion of a slit has a greater width than a downstream portion thereof, and the force by which the sheet material is pulled into the slit will unlikely be excessive, and the sheet material on the contact surface will smoothly move into the slit in an upstream portion of the slit. On the other hand, a downstream portion of the slit has a small width, and the force by which the sheet material is pulled into the suction space from the slit to stretch the protruding portion will be larger in the downstream portion of the slit than in the upstream portion of the slit.

Preferably, the carrying device carries the first sheet material and a second sheet material different from the first sheet material in parallel to each other, and further includes a body transferring section configured to place an absorbent body so as to bridge between the first and second sheet materials at a position of a downstream half of the inclined slit portion in the relative direction and/or a downstream slit portion that is continuous with a downstream end of the inclined slit portion in the relative direction.

In this case, an absorbent body can be attached to protruding portions whose shape is stable, and the force of attachment will therefore not vary and there will be obtained aesthetically pleasing worn articles.

The method of the present invention may further include the step of performing a predetermined process on the protruding portion being stretched (drawn) in the width direction.

In this case, since the protruding portion is stretched in the width direction, the protruding portion can easily be processed.

In the present invention, the predetermined process may be performed by bonding another object on the protruding portion being stretched.

The other object may be a tape, a fastener, a flap, or the like, as well as an absorbent body.

Note that the predetermined process may be severing or layering.

In the carrying method of the present invention, the first sheet material and a second sheet material different from the first sheet material are carried in parallel to each other, wherein the predetermined process is performed by placing an absorbent body so as to bridge between the first and second sheet materials at a position of a downstream half of the inclined slit portion in the relative direction and/or a downstream slit portion that is continuous with a downstream end of the inclined slit portion in the relative direction.

In this case, an absorbent body can be placed and attached to the protruding portion of the first sheet material having a stable shape, and it is therefore possible to improve the quality of the worn article.

Preferably, a force by which the edge is sucked into the slit portion is greater than a force by which the protruding portion is shrunk in the width direction.

In this case, the creases of the protruding portion will easily be straightened.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Prior to the description of embodiments of the present invention, an example structure of a worn article 1 will be outlined with reference to the drawings.

As shown in FIG. 1C, the worn article 1 includes an absorbent body 2, and a pair of (front and back) around-torso members 3 and 3. The absorbent body 2 includes a front portion 20, a back portion 21, and a crotch portion 22. The front portion 20 extends in the girth direction X1 covering the front torso (the front portion of the torso) of the wearer. The back portion 21 extends in the girth direction X1 covering the back torso (the back portion of the torso) of the wearer. The crotch portion 22 covers the crotch of the wearer between the front portion 20 and the back portion 21.

The crotch portion 22 is continuous with the front portion 20 and the back portion 21, and extends in a longitudinal direction Y perpendicular to the girth direction X1. The absorbent body 2 forms a part or whole of the crotch portion 22.

The present worn article is worn while the crotch portion 22 is folded in two along a virtual line parallel to the girth direction X1. Thus, end portions in the girth direction X1 of the front around-torso member 3 and those of the back around-torso member 3 are laid on each other.

An absorbent core (not shown) may be provided in the absorbent body 2. A cuff may be provided on a top sheet (not shown) covering the skin-contact surface of the absorbent core.

The absorbent body 2 is placed so as to bridge between the front around-torso member 3 and the back around-torso member 3. That is, the front portion 20, which is one end portion in the longitudinal direction Y of the absorbent body 2, is bonded to the front around-torso member 3. On the other hand, the back portion 21, which is the other end portion in the longitudinal direction Y of the absorbent body 2, is bonded to the back around-torso member 3.

Each around-torso member 3 is made of a laminate including torso and leg elastic members F1 and F2 sandwiched between a pair of webs W1 and W2.

The elastic members F1 and F2 are sandwiched between the pair of webs W1 and W2, and are stretchable in the girth direction X1. The elastic members F1 and F2 may be cut off at the center in the girth direction X1.

When the worn article is a diaper, a male touch fastener (not shown) may be secured to the back around-torso member 3, and a female touch fastener (not shown) may be secured to the front around-torso member 3.

Note that a tape material with a fastening agent applied thereon may be used instead of the male touch fastener, in which case the front around-torso member 3, or the like, needs to be provided with a surface on which the fastening agent adheres easily.

When the worn article is pants-shaped, the end portion in the girth direction X1 of the front around-torso member 3 and that of the back around-torso member 3 may be welded to each other.

Next, an example method for manufacturing the diaper will be outlined.

As shown in FIG. 1A, while carrying a pair of band-shaped webs (an example of the sheet material) W1 and W2 that are continuous in the carrying direction X and have a first lateral edge L1 and a second lateral edge L2, the linear-shaped torso elastic member F1 and the wave-shaped leg elastic member F2 are layered together and sandwiched between the webs W1 and W2. The leg elastic member F2 is placed between the webs W1 and W2, being carried, so as to be continuous in the longitudinal direction of the webs W1 and W2 and along a waveform having a predetermined wavelength, thereby producing a composite sheet W.

Note that at positions where the elastic members F1 and F2 are not needed, the shrinking force of the elastic members may be nullified by cutting or melting the elastic members.

The composite sheet W, being carried, is severed along a virtual severing line C that is continuous in the longitudinal direction of the composite sheet and has a waveform that is in synchronism with the above-mentioned waveform and that has a wavelength equal to the above-mentioned wavelength. Thus, the composite sheet W is divided into a first divided sheet (an example of the sheet material) S1 that has the first lateral edge L1 and has depressed portions 42 and protruding portions 41 alternating with each other along the severing line C, and a second divided sheet (an example of the sheet material) S2 that has the second lateral edge L2 and has protruding portions 41 and depressed portions 42 alternating with each other along the severing line C. The first and second divided sheets S1 and S2 are provided with a first and a second medial edges M1 and M2 (FIG. 1B), respectively, extending along the severing line C.

Note that the amplitude of the waveform of the leg elastic member F2 may be the same as, or different from, the amplitude of the waveform of the severing line C.

After the division, the two divided sheets S1 and S2 are moved relative to each other in the width direction Y perpendicular to the carrying direction X so that the width from the first lateral edge L1 to the second lateral edge L2 is widened, i.e., so that the first medial edge M1 and the second medial edge M2 move apart from each other, as shown in FIG. 1B.

Also, after the division, the phase of the first divided sheet S1 and that of the second divided sheet S2 in the carrying direction X are shifted from each other so that the protruding portions 41 of the divided sheet S1 oppose those of the divided sheet S2. Then, the absorbent body 2 is placed so as to bridge between the protruding portion 41 of the first divided sheet S1 and the protruding portion 41 of the second divided sheet S2.

With the absorbent body 2 placed thereon, the pair of divided sheets S1 and S2 and the absorbent body 2 become a continuous laminate R. The continuous laminate R is severed along the virtual severing line CL extending in the width direction Y perpendicular to the carrying direction X, producing individual diapers. Note that prior to the severing, the continuous laminate R may be folded so that the divided sheets S1 and S2 are laid on each other.

Next, an example of a carrying device, which is an important part of the present embodiment, will be described.

As shown in FIG. 4A, the present carrying device may include a pair of crease straightening (smoothing) sections 60 and 60 between a pair of rollers 50 and 51, for example.

Each crease straightening section 60 includes a carrying section 61 and a box 62. In the present embodiment, the carrying section 61 is formed by one or more plates, and forms a part of the box 62.

Figure 6A:
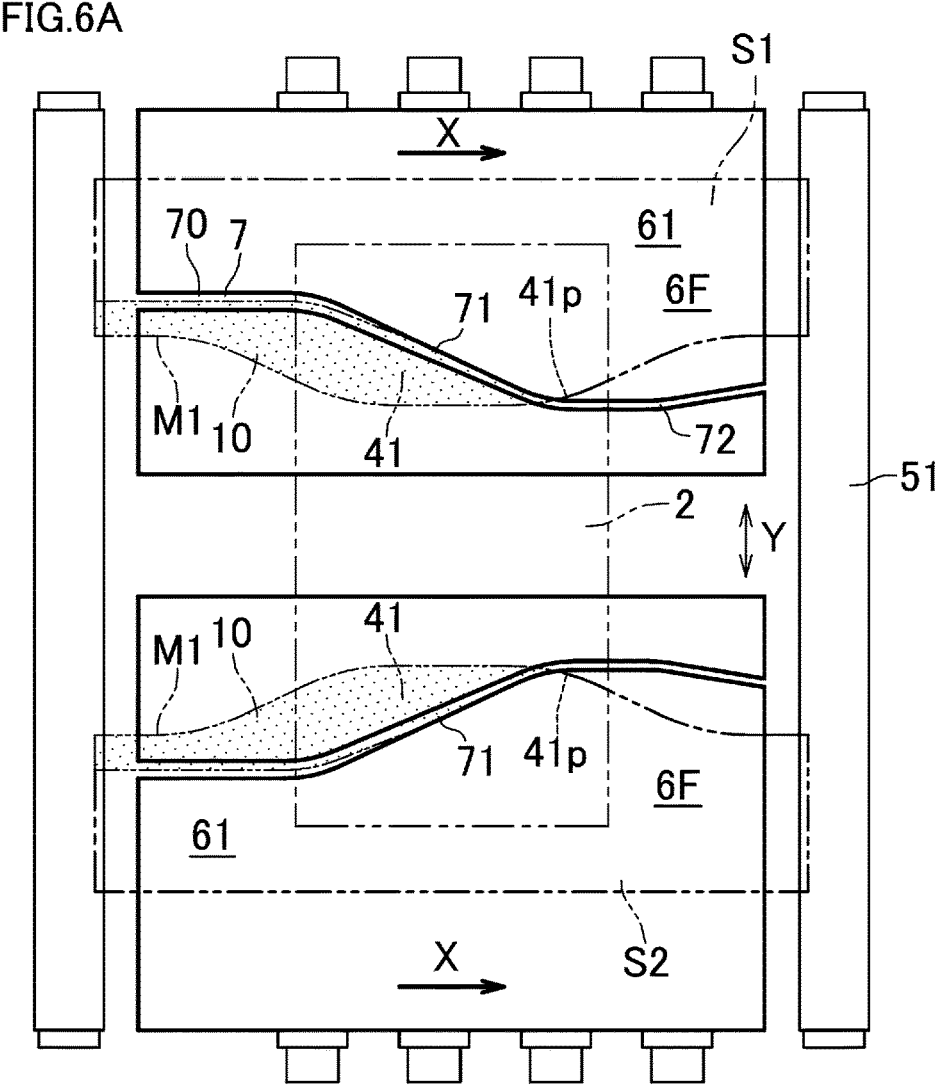
FIG. 6A and FIG. 6B are a schematic plan view and side view, respectively, showing the carrying device.
Figure 6B:
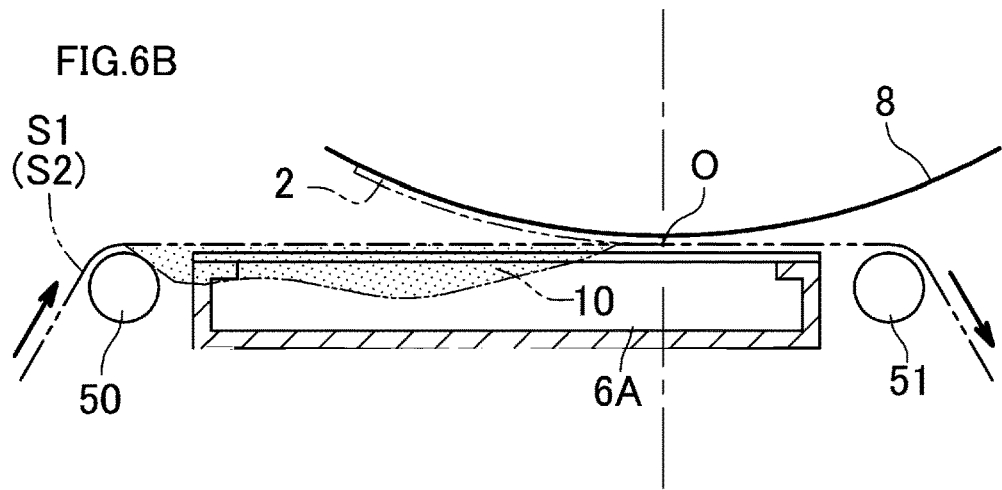

In FIG. 4B, a body transferring section including a drum 8, for example, is placed at a position opposing the carrying section 61. The drum 8 carries the absorbent body 2 as shown in FIG. 6B and FIG. 7B, and places the absorbent body 2 on the pair of divided sheets S1 and S2 as shown in FIG. 6A and FIG. 8B.

Each carrying section 61 of FIG. 4A includes a contact surface 6F that is to be in contact with one surface of one of the divided sheets S1 and S2. A single line of slit 7, for example, is formed on the contact surface 6F of each carrying section 61. The slit 7 extends in the carrying direction X from one end to the other end of the carrying section 61. The slit 7 includes an inclined slit portion 71, an upstream slit portion 70 continuous with the upstream end of the inclined slit portion 71, and a downstream slit portion 72 continuous with the downstream end of the inclined slit portion 71.

Figure 3A:
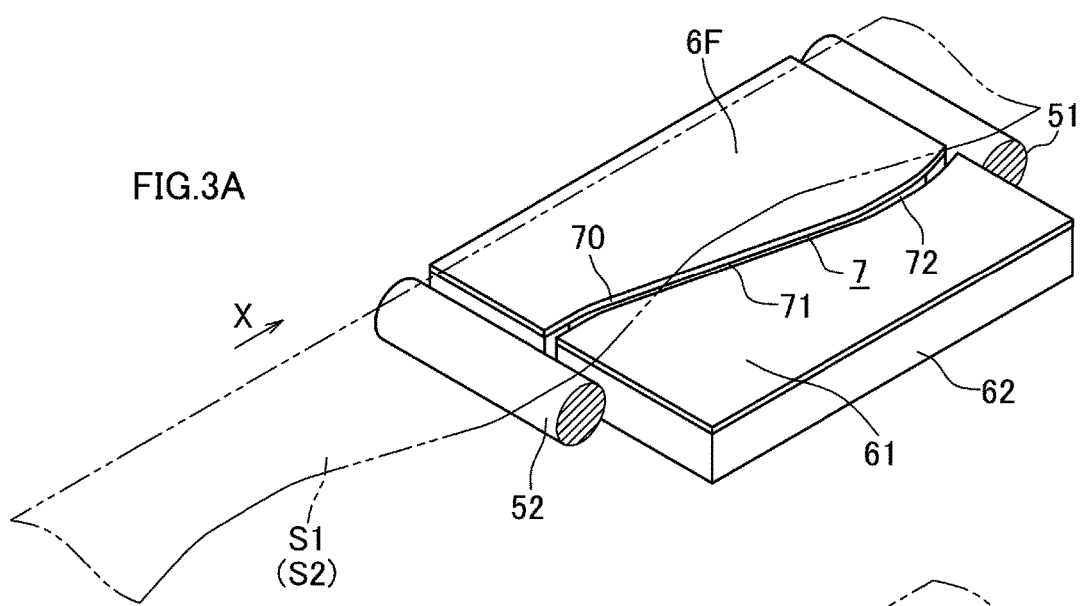
FIG. 3A and FIG. 3B are schematic perspective views each showing a portion of the carrying device.
Figure 3B:
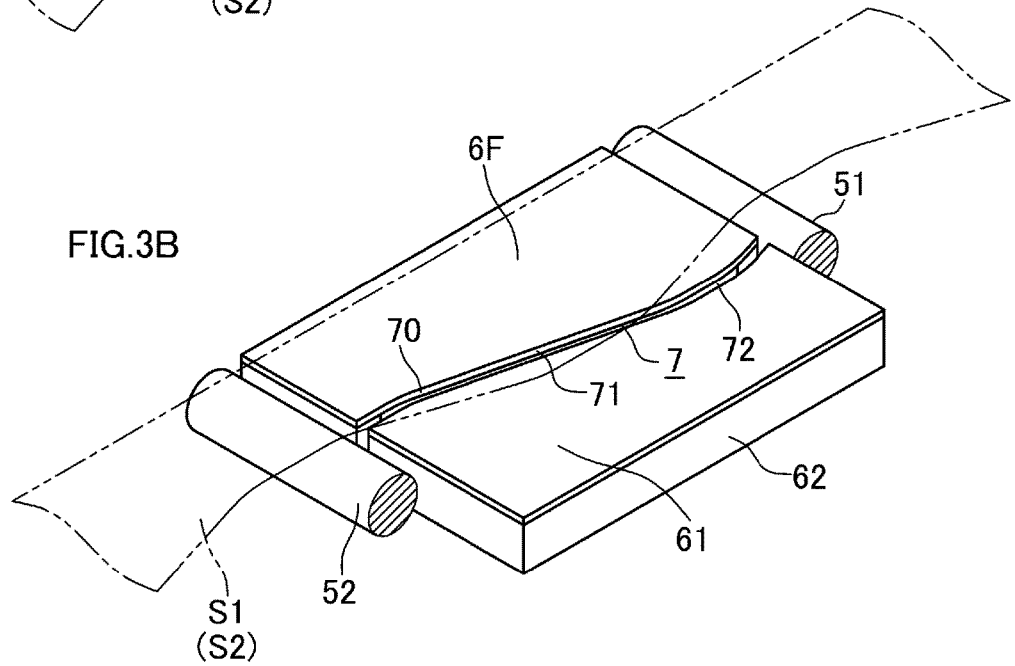
Figure 3C:
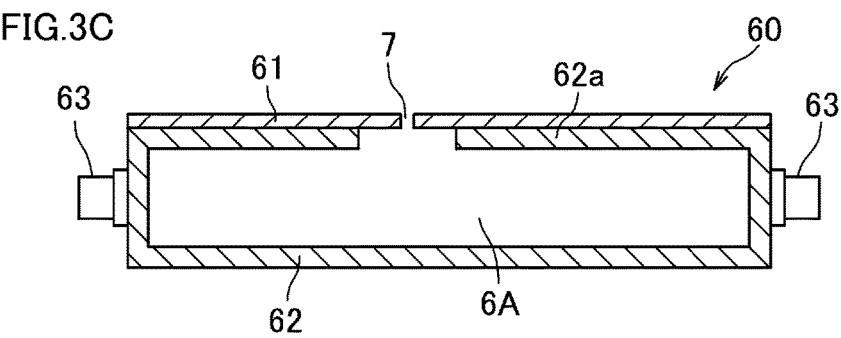
FIG. 3C is a cross-sectional view showing the same.

As clearly shown in FIG. 3A to FIG. 3C, the slit 7 divides each carrying section 61 into a plurality of pieces. Each carrying section 61 is secured onto the main part of the box 62 by means of a fastening means such as a bolt (not shown). This allows for the carrying sections 61 to be replaced to change the shape or position of the slit 7.

As shown in FIG. 4A, the upstream slit portion 70 and/or the inclined slit portion 71 may have a width D that decreases from the upstream side to the downstream side in the carrying direction X.

A plurality of suction pipes 63, for example, may be connected to each box 62. The suction pipes 63 are in communication with a suction space 6A and a negative pressure source (not shown) in order to maintain a negative pressure in the suction space 6A inside the box 62 of FIG. 4B.

The suction space 6A is open along the slit 7 and keeps the slit 7 under a negative pressure so that the first or second medial edge M1, M2 of the divided sheet S1, S2 is pulled (sucked) into the slit 7 and pulled further into the suction space 6A via the slit 7.

Note that in FIG. 4A to FIG. 7B, only a portion of each divided sheet S1, S2 for a single worn article is shown in a two-dot chain line, and a sucked portion 10 thereof to be pulled into the slit 7 is dotted.

Figure 5A:
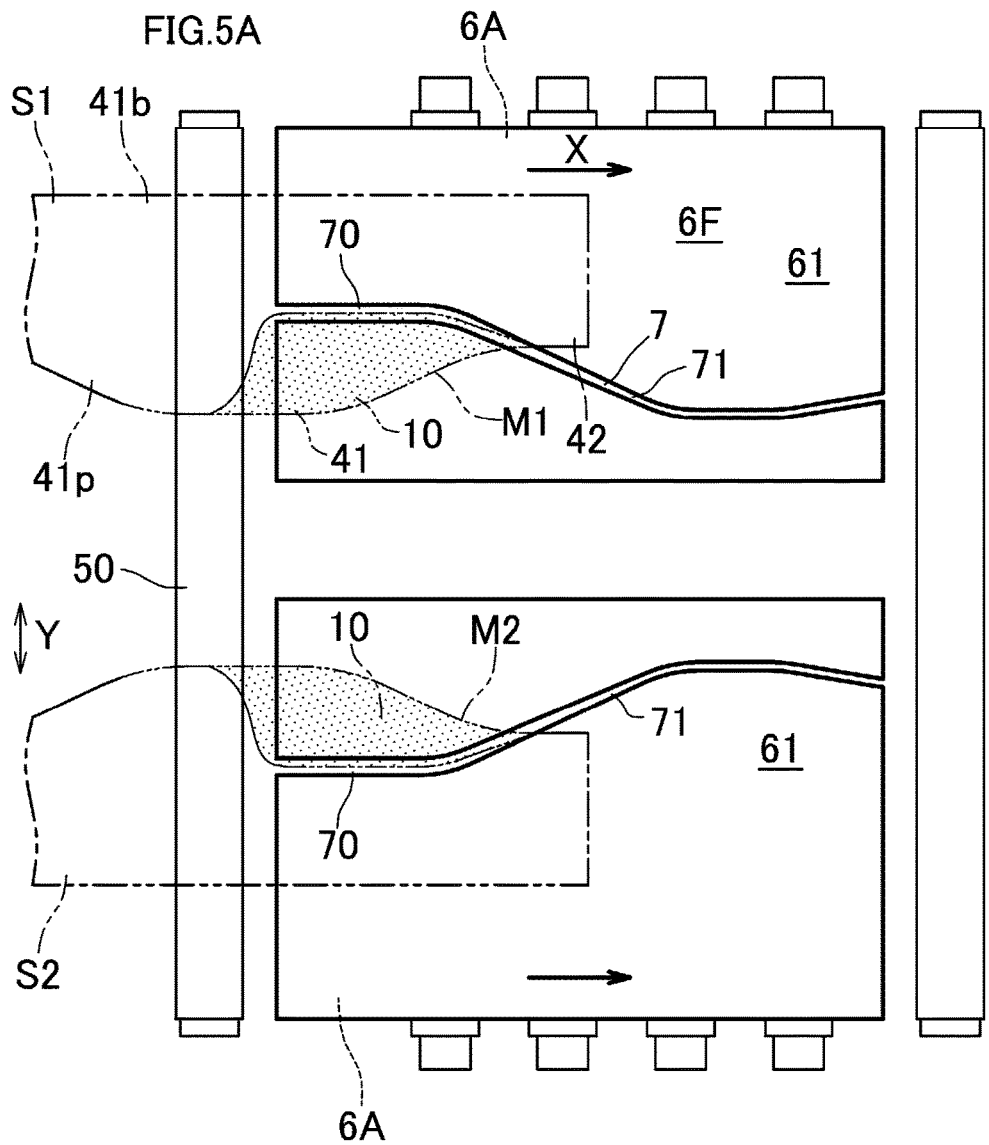
FIG. 5A and FIG. 5B are a schematic plan view and side view, respectively, showing the carrying device.

The upstream slit portion 70 of FIG. 4A extends in parallel to the carrying direction X, for example, and sucks in the medial edge M1, M2 of the depressed portion 42 of FIG. 4A and FIG. 6A or the medial edge M1, M2 of the protruding portion 41 of FIG. 5A so that these portions are pulled into the upstream slit portion 70 and the suction space 6A.

Figure 7A:
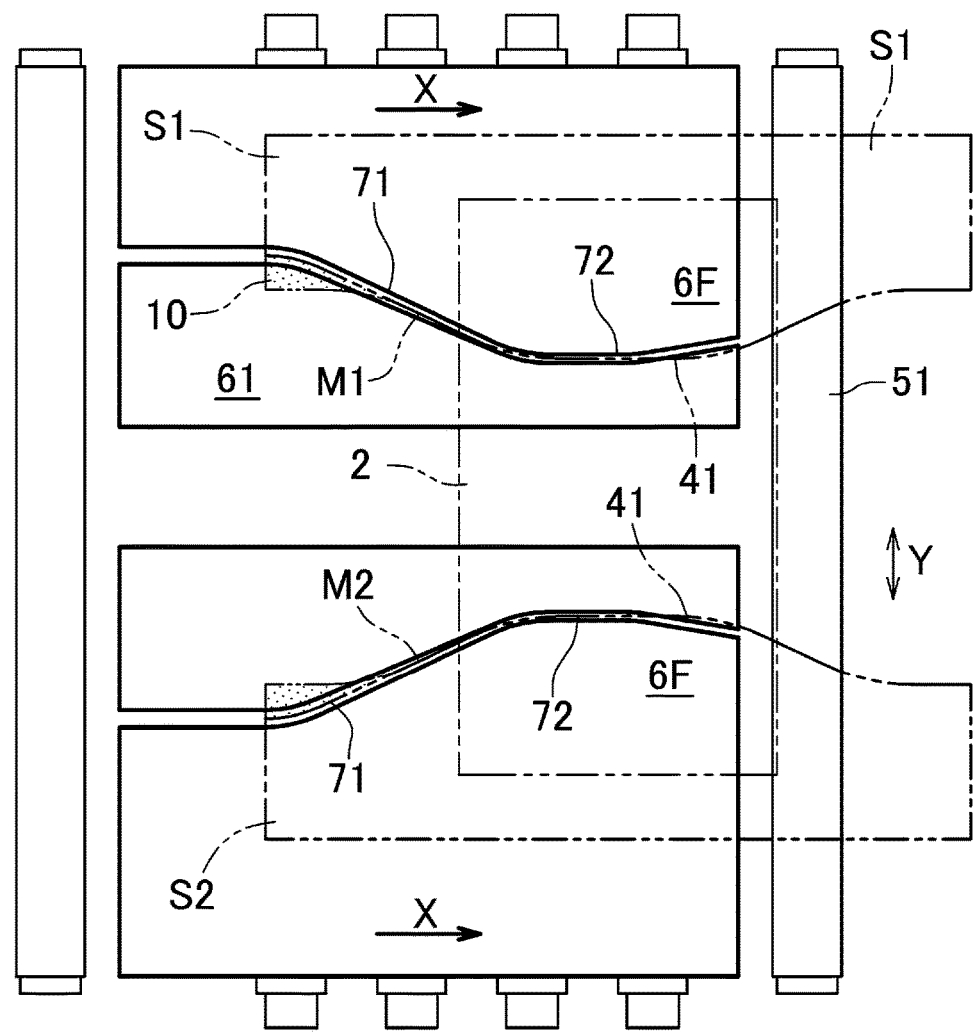
FIG. 7A and FIG. 7B are a schematic plan view and side view, respectively, showing the carrying device.
Figure 7B:
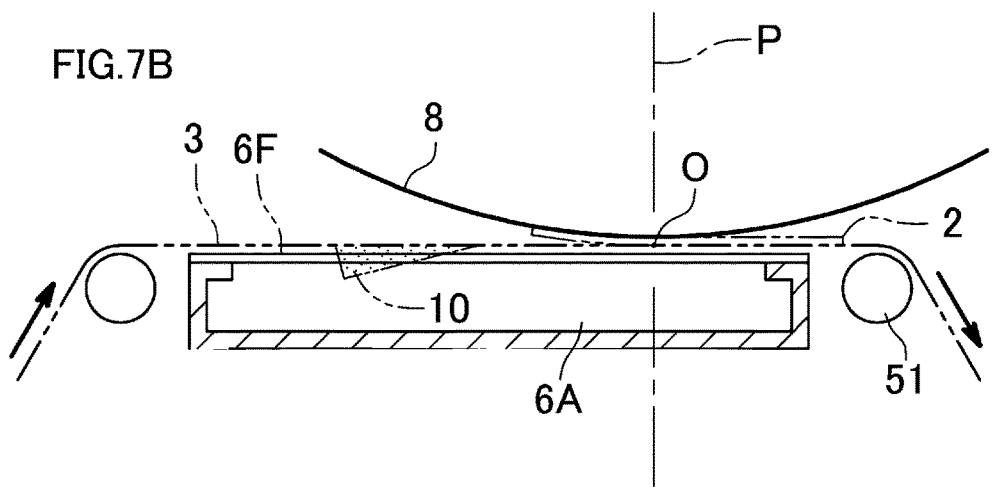

Each inclined slit portion 71 extends in an inclined direction so as to be displaced from a proximal side 41b toward a distal side 41p of the protruding portion 41 while extending downstream in the carrying direction X, and sucks in the medial edge M1, M2 of the protruding portion 41 as shown in FIG. 6A and FIG. 7A. By virtue of this suction, the medial edge M1, M2 of the protruding portion 41 is pulled into the inclined slit portion 71 and the suction space 6A.

As shown in FIG. 6A and FIG. 7A, each downstream slit portion 72 is shaped in conformity to the medial edge M1, M2 of the protruding portion 41 of the divided sheet S1, S2. Therefore, the portion of the divided sheet S1, S2 that has been pulled into the inclined slit portion 71 and the suction space 6A via the inclined slit portion 71 emerges onto the contact surface 6F of the carrying section 61 at the downstream slit portion 72. Note that each downstream slit portion 72 may include a parallel portion that extends in parallel to the carrying direction X and an inclined portion that has an inclination in the opposite direction to that of the inclined slit portion 71.

The drum 8 (FIG. 7B) places the absorbent body 2 so as to bridge between a pair of sheet materials S1 and S2, being carried in parallel to each other, at the position P (FIG. 7B) where the downstream half of the inclined slit portion 71 or the downstream slit portion 72 is provided.

As indicated by a solid line and a two-dot chain line of FIG. 2, the box 62 of the crease straightening section 60 is rotatable about the upstream end portion. This allows for replacement of the divided sheets S1 and S2 and maintenance.

As shown in FIG. 3C, the carrying section 61 may be supported by a long and thick reinforcement arm 62a of the box 62.

Next, an example of a carrying method, which is an important part of the present embodiment, will be described.

As indicated by a two-dot chain line of FIG. 3A and FIG. 3B, the divided sheet S1 (S2) is continuously carried while being kept under a tension in the carrying direction X of the divided sheet S1 (S2). In the present embodiment, as shown in FIG. 4A to FIG. 7A, the first and second divided sheets S1 and S2 are carried in parallel to each other with the medial edges M1 and M2 thereof opposing each other.

Note that although FIG. 3A, FIG. 3B and FIG. 4A to FIG. 8A each show a developed view as if the divided sheet S1 (S2) were carried along a single plane, the divided sheet S1 (S2) is in practice carried while being bent at a pair of rollers 50 and 51 as shown in FIG. 4B.

As shown in FIG. 1B, each divided sheet S1, S2 includes the elastic members F1 and F2. Particularly, each protruding portion 41 includes the elastic member F2 placed along the medial edge M1, M2, and the protruding portion 41 is therefore carried while being shrunk in the width direction Y.

On the other hand, the slit 7 shown in FIG. 4A to FIG. 7A is under a negative pressure via the suction space 6A. Due to this negative pressure, the medial edge M1, M2 of the sucked portion 10, being carried, is sucked into the slit 7 with a sucking force that is greater than the force by which the protruding portion 41 is shrunk in the width direction Y.

As shown in FIG. 4A, when the depressed portion 42 of the divided sheet S1, S2 moves past the upstream roller 50 to reach the carrying section 61, the sucked portion 10 on the medial edge M1, M2 side of the depressed portion 42 is sucked and pulled into the slit 7 and the suction space 6A via the upstream slit portion 70. That is, as shown in FIG. 4B, the sucked portion 10 is pulled into the upstream slit portion 70 (FIG. 4A) and the suction space 6A so that the divided sheet S1, S2 is bent along the upstream slit portion 70.

Figure 5B:
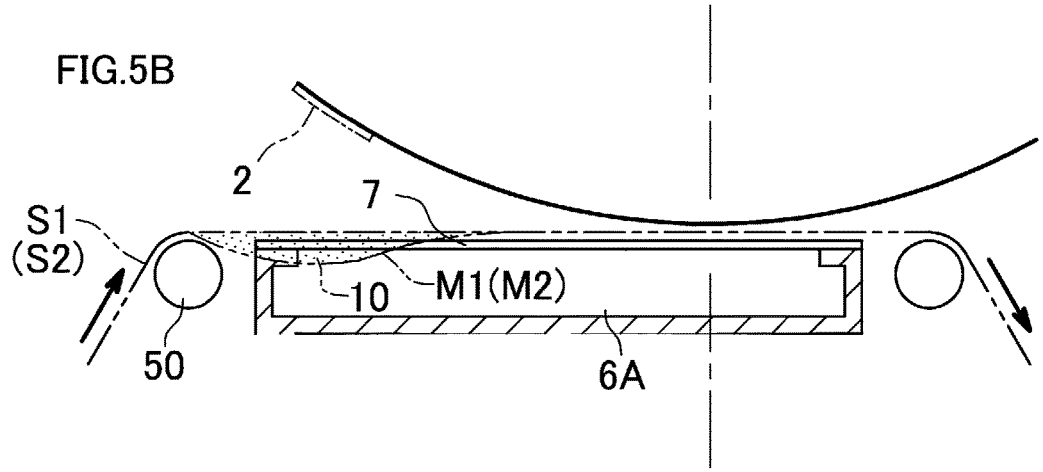

Then, as shown in FIG. 5A, when the protruding portion 41, shrunk in the width direction Y of the divided sheets S1 and S2, moves past the upstream roller 50 to reach the carrying section 61, the sucked portion 10 on the medial edge M1, M2 side of the protruding portion 41 is sucked and pulled into the slit 7 and the suction space 6A via the upstream slit portion 70. That is, as shown in FIG. 5B, the sucked portion 10 is pulled into the upstream slit portion 70 (FIG. 5A) and the suction space 6A so that the divided sheet S1, S2 is bent along the upstream slit portion 70.

As shown in FIG. 5A, when the depressed portion 42 of the divided sheet S1, S2 moves past the upstream slit portion 70 to reach the inclined slit portion 71, the portion of the depressed portion 42 that has been pulled into the slit 7 and the suction space 6A emerges onto the contact surface 6F of the carrying section 61.

Then, as shown in FIG. 6A, the divided sheets S1 and S2 are carried, and the protruding portion 41 moves past the inclined slit portion 71. The portion that has moved past the inclined slit portion 71 emerges onto the contact surface 6F of the carrying section 61 via the inclined slit portion 71. At this point, as the distal side 41p of the protruding portion 41 is received by the downstream end portion of the inclined slit portion 71, the protruding portion 41 is stretched in the width direction Y perpendicular to the carrying direction X.

As shown in FIG. 6B, at the point O of attachment, the absorbent body 2 starts to be attached (bonded or welded) between the protruding portions 41 and 41, which are being stretched in the width direction Y. Note that at a position upstream of the point O of attachment, a portion of the protruding portion 41 is pulled into the inclined slit portion 71 and the suction space 6A via the slit 7.

As the divided sheets S1 and S2 are carried further, as shown in FIG. 7A, the entire protruding portion 41 emerges onto the contact surface 6F of the carrying section 61 via the inclined slit portion 71, and the medial edge M1, M2 of the protruding portion 41 is drawn toward the inclined slit portion 71 and the downstream slit portion 72, thus keeping creases on the protruding portion 41 straightened.

At the point O of attachment, the absorbent body 2 continues to be attached between the protruding portions 41 and 41, which are being stretched in the width direction Y, as shown in FIG. 7B. Then, the absorbent body 2 is attached to the divided sheets S1 and S2 over the entire extent in the girth direction X1. Thus, the continuous laminate R is carried downstream past the roller 51 with creases on the protruding portion 41 being stretched.

Next, another embodiment of the present invention will be described with reference to FIG. 8A to FIG. 12B.

The present embodiment is directed to a case in which a pants-type diaper is manufactured from the continuous laminate R as shown in FIG. 1B.

Prior to the description of the carrying method and the carrying device, the structure of the diaper of the present embodiment will be described.

Referring to FIG. 12A and FIG. 12B, in the present embodiment, the absorbent body 2 is placed so as to bridge between the depressed portion 42 of a front around-torso member 3F and the protruding portion 41 of a back around-torso member 3B. On the other hand, as shown in the developed view of FIG. 12A and in FIG. 12B, the front and back around-torso members 3F and 3B may be of the same height (width) at the opposite end portions thereof along which the front and back around-torso members 3F and 3B are sealed together.

That is, the opposite end portions of the front around-torso member 3F are formed by the protruding portion 41, and the opposite end portions of the back around-torso member 3B are formed by the depressed portion 42.

Next, the carrying device will be described.

Figure 9:
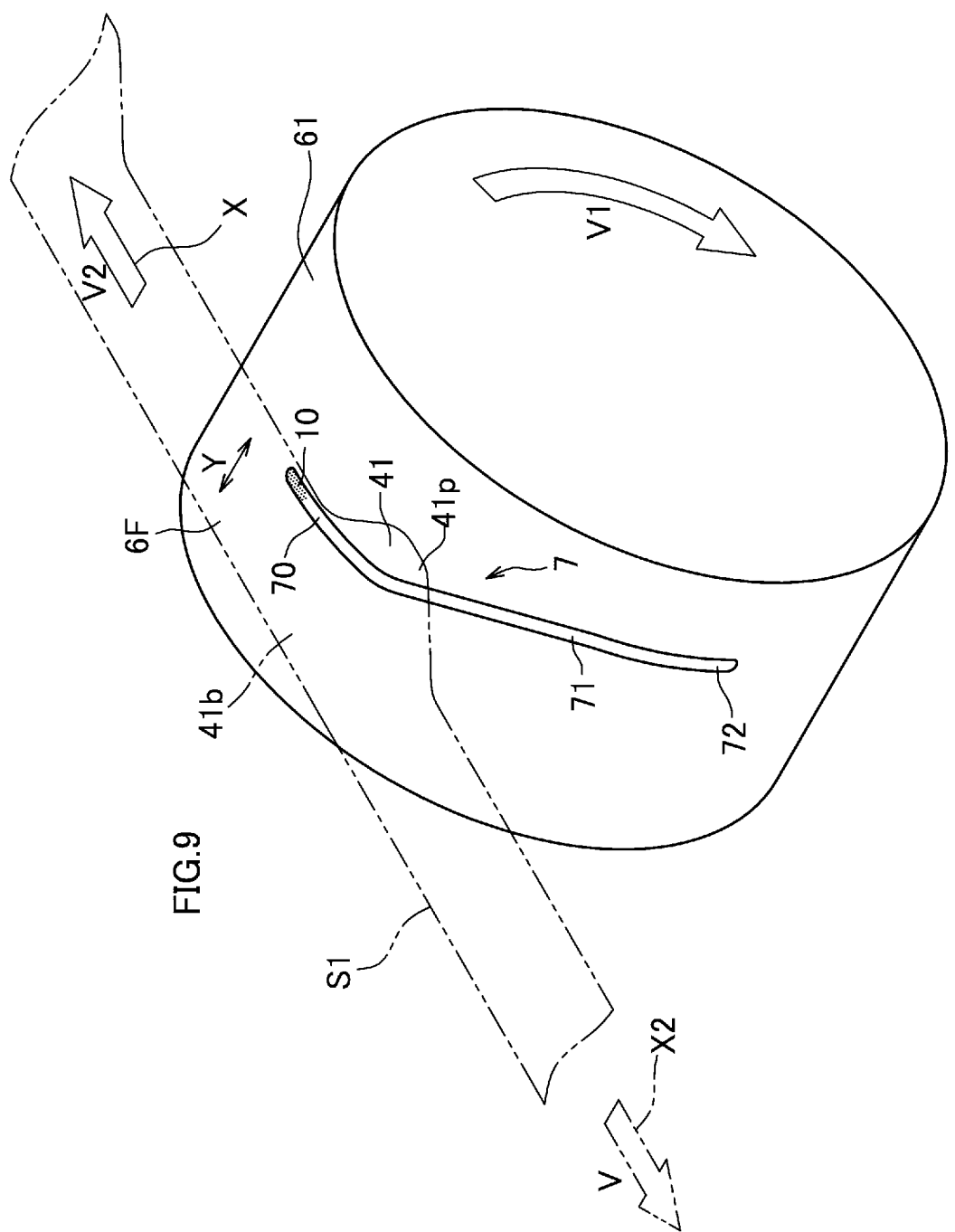
FIG. 9 is a schematic perspective view showing a portion of the carrying device.

As shown in FIG. 9, the present carrying section 61 is formed by a drum. As shown in FIG. 10, the present carrying section 61 rotates at the circumferential velocity V as shown in FIG. 9 by the driving force from a drive shaft 64. The tangential direction of the circumferential velocity V is equal to the direction of the carrying velocity V2 of the first divided sheet S1, and the circumferential velocity V is greater than the carrying velocity V2. Therefore, the direction X2 of the relative velocity V (relative direction) of the divided sheet S1 with respect to the contact surface 6F of the carrying section 61 is opposite to the actual carrying direction X, as indicated by a phantom line.

Note that the divided sheet S1 comes into contact with the contact surface 6F approximately in a linear contact.

As shown in FIG. 10, the carrying section 61 is formed by a hollow cylinder. The box 62 and a duct as the suction pipe 63 are placed inside the carrying section 61. The box 62 and the suction pipe 63 may not be rotatable but may be secured to a frame (not shown).

Note that in FIG. 10, the slit 7 is shown as being developed and is indicated by a two-dot chain line.

In the present embodiment, the slit 7 of FIG. 9 is formed on the cylinder (drum), and extends in an inclined direction so as to be displaced from the proximal side 41b toward the distal side 41p of the protruding portion 41 while extending in the relative direction X2 in which it travels relative to the contact surface 6F of the first divided sheet S1.

Next, an example of a manufacturing method will be described with reference to FIG. 8.

First, as in the above-described embodiment, the absorbent bodies 2 are placed successively so as to bridge, in the width direction Y, between the first divided sheet S1 and the second divided sheet S2, thus producing the continuous laminate R. The folding step, the first crease straightening step, the first attachment step, the second crease straightening step, the second attachment step and the severing step to be described below are performed repeatedly while the continuous laminate R is carried in the carrying direction X, which extends along the direction in which the first and second divided sheets S1 and S2 are continuous.

In the folding step, the continuous laminate R is folded in two at the absorbent body 2 so that the first divided sheet S1 and the second divided sheet S2 are laid on each other.

Due to the protruding shapes/depressed shapes and the tension from the elastic member F2 formed on the first divided sheet S1, the first divided sheet S1 is creased, and the protruding portion 41 of the first divided sheet S1 indicated by a two-dot chain line is therefore shrunk significantly in the width direction Y as indicated by a solid line. Therefore, the folding is performed while the medial edges M1 and M2 of the pair of divided sheets S1 and S2 are misaligned with each other at the central portion between adjacent absorbent bodies 2 and 2, i.e., at a position to be the end portion 3E of each worn article.

As the protruding portion 41 is shrunk in the width direction Y, the first divided sheet S1 is shrunk in the width direction Y. Therefore, the folding is performed while the lateral edges L1 and L2 of the pair of divided sheets S1 and S2 are misaligned with each other.

Thus, immediately after the folding in two, the edges are misaligned both on the waist side and on the leg hole side.

On the other hand, a negative pressure is acting along the slit 7 of FIG. 9 and FIG. 10 via the suction space 6A. Due to this negative pressure, the sucked portion 10 on the medial edge M1 side of the first divided sheet S1 is sucked into the slit 7 with a sucking force that is greater than the force by which the protruding portion 41 is shrunk in the width direction Y, while the first divided sheet S1 is carried. Due to this suction, the protruding portion 41, which has been shrunk, is stretched as will be described below.

Figure 11A:
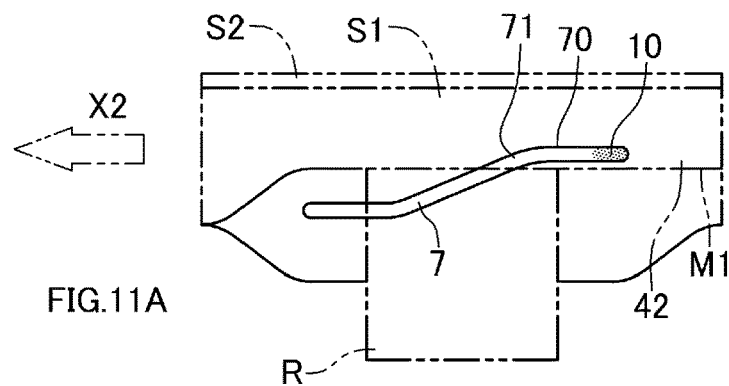
FIG. 11A, FIG. 11B, FIG. 11C and FIG. 11D are developed views showing a method of straightening creases by the carrying device.

As shown in FIG. 11A, when the depressed portion 42 of the divided sheet S1 reaches the upstream slit portion 70, the sucked portion 10 on the medial edge M1 side of the depressed portion 42 is sucked into and held against the slit 7 via the upstream slit portion 70.

Note that in FIG. 9 to FIG. 11D, the sucked portion 10, being sucked into the slit 7, is dotted.

Then, when the protruding portion 41 of the first divided sheet S1, being shrunk in the width direction Y, reaches the upstream slit portion 70, the sucked portion 10 on the medial edge M1 side of the protruding portion 41 is sucked into and held against the upstream slit portion 70, with the sucked portion 10 being slightly inside the upstream slit portion 70.

Figure 11B:
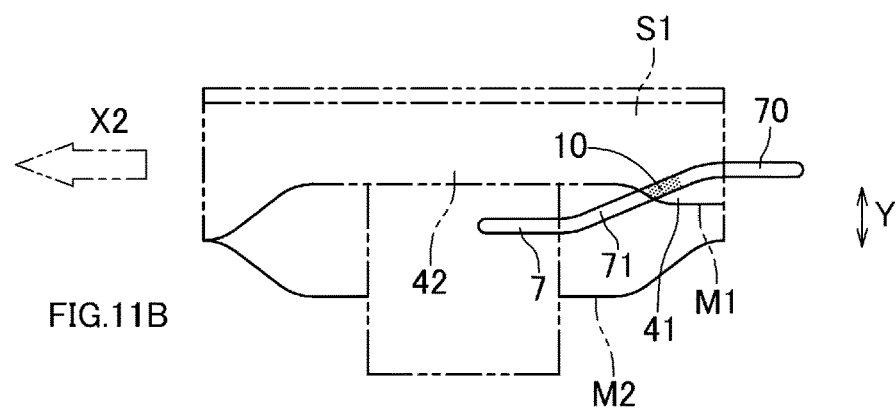

As shown in FIG. 11B, when the depressed portion 42 of the first divided sheet S1 moves past the upstream slit portion 70 and the protruding portion 41 reaches the inclined slit portion 71, the portion of the depressed portion 42, which has been held against the slit 7, comes off the slit 7 and off the contact surface 6F of the carrying section 61 of FIG. 9.

Figure 11C:
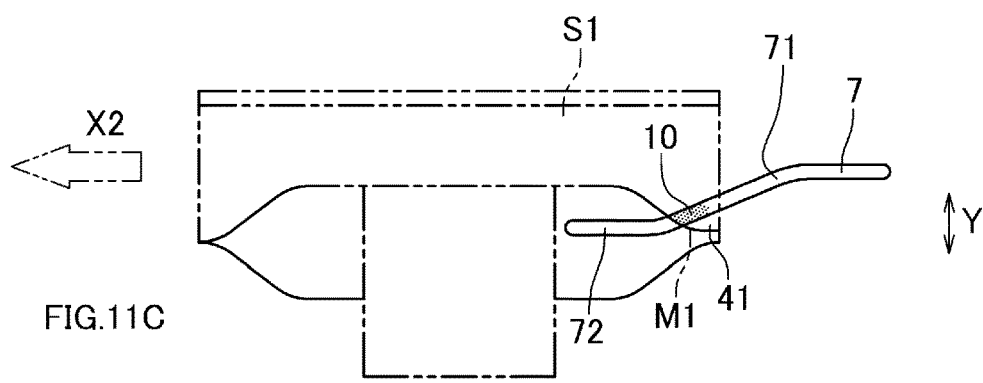
Figure 11D:
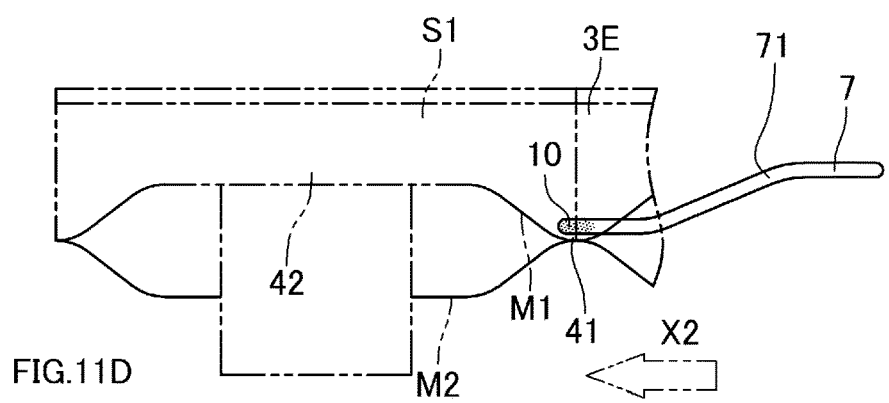

Then, as shown in FIG. 11C, as the first divided sheet S1 is carried, the protruding portion 41 moves past the inclined slit portion 71. The portion that has moved past the inclined slit portion 71 comes off the inclined slit portion 71 and off the contact surface 6F of the carrying section 61 of FIG. 9. At this point, the portion of the first divided sheet S1, which is held against the inclined slit portion 71, is displaced in the width direction Y, thereby stretching the protruding portion 41 in the width direction Y perpendicular to the relative direction X2 of FIG. 11D.

Referring to FIG. 8B, in the first attachment step, after the stretching, the divided sheets S1 and S2 are attached together intermittently in the carrying direction X, as indicated by dotting, at the position to be the end portion 3E of each worn article and at the medial edges M1 and M2 to be leg holes 23 of the worn article 1.

Then, the first lateral edge L1 of the first divided sheet S1 of the continuous laminate R is carried while being in contact with inclined rollers (not shown). On the other hand, the second lateral edge L2 of the second divided sheet S2 of the continuous laminate R is carried while being in contact with hold rollers (not shown). Therefore, in the second crease straightening step, the first lateral edge L1 of the first divided sheet S1 is carried in an inclined direction by the inclined rollers, straightening the creases on the first divided sheet S1 in the width direction Y. Thus, the lateral edges L1 and L2 of the divided sheets S1 and S2 are aligned together or close together.

In the second attachment step, with the creases being straightened, the first divided sheet S1 and the second divided sheet S2 are attached successively at different positions, along one of the end portions 3E (one end), across the extent from the medial edge M1, M2 to the lateral edge L1, L2.

Note that after or during the attachment, the continuous laminate R is severed into individual pairs of pants.

The device and the method of the present invention can be applicable if at least one of the sheet materials has a wave-shaped pattern. For example, the worn article may be T-shaped, rather than H-shaped. Moreover, the edge of the wave-shaped pattern may form the upper edge of the worn article. Furthermore, the sheet material may be an intermediate product or a finished product of an article other than a worn article.

The pair of edges of a single sheet material may be in a wave-shaped pattern. In such a case, the pair of edges may extend parallel to each other, or the pair of edges may be in asymmetry with each other. In these cases, a pair of slits or a pair of inclined slit portions extending in the carrying direction may be provided for a single sheet material. For example, the sheet material may be one including a plurality of absorbent bodies continuous with each other in the longitudinal direction.

The sheet material does not need to be one obtained by dividing a single sheet material into two pieces.

The contact surface may be formed by a resin having a small coefficient of friction, e.g., a panel of polytetrafluoroethylene.

While preferred embodiments have been described above with reference to the drawings, various obvious changes and modifications will readily occur to those skilled in the art upon reading the present specification.

For example, articles to be manufactured by the present manufacturing method may include such worn articles as masks, as well as diapers.

The elastic members may be absent.

Guide rolls may be placed before and after the carrying section, guiding the sheet material in the width direction.

Thus, such variations and modifications shall fall within the scope of the present invention as defined by the appended claims.

INDUSTRIAL APPLICABILITY

The present invention is applicable to a device and a method for carrying a sheet material of a disposable worn article such as a diaper, pants, a feminine sanitary product or a mask.

REFERENCE SIGNS LIST

1: Worn article, 10: Sucked portion
2: Absorbent body, 20: Front portion, 21: Back portion, 22: Crotch portion
3: Around-torso member, 3B: Back around-torso member, 3F: Front around-torso member, 3E: End portion
41: Protruding portion, 41b: Proximal side, 41p: Distal side, 42: Depressed portion
50, 51: Roller
6A: Suction space, 6F: Contact surface, 60: Crease straightening section, 61: Carrying section, 62: Box
62a: Reinforcement arm, 63: Suction pipe, 64: Drive shaft
7: Slit, 70: Upstream slit portion, 71: Inclined slit portion, 72: Downstream slit portion
8: Drum (body transferring section)
C: Severing line, P: Position
F1, F2: Elastic member
L1: First lateral edge, L2: Second lateral edge
M1: First medial edge, M2: Second medial edge
R: Continuous laminate, S1, S2: Divided sheet (sheet material), W: Composite sheet
V: Relative velocity, V1: Circumferential velocity, V2: Carrying velocity
X: Carrying direction, X1: Girth direction, X2: Relative direction, Y Width direction

The invention claimed is:

1. A method for carrying a sheet material of a worn article using a carrying device, the carrying device comprising:
a carrying section having a contact surface to be in contact with one surface of a first sheet material that is continuous in a carrying direction, wherein at least one edge of the first sheet material is wave-shaped so as to repeatedly define a protruding portion and a depressed portion,
the carrying section defining an inclined slit portion, wherein the inclined slit portion defines an opening on the contact surface, wherein the inclined slit portion extends in an inclined direction so as to be displaced from a proximal side toward a distal side of the protruding portion while extending in a relative direction in which the first sheet material moves relative to the contact surface, and wherein the inclined slit portion sucks at least a portion of the protruding portion along the wave-shaped edge; and a box defining a suction space that is continuous with the inclined slit portion and keeps the inclined slit portion under a negative pressure so as to suck the protruding portion of the first sheet material so that the at least a portion of the protruding portion is pulled into the inclined slit portion, the method comprising the steps of:

continuously carrying the first sheet material while keeping the first sheet material under a tension in the carrying direction of the first sheet material;

sucking the wave-shaped edge into the inclined slit portion while carrying the first sheet material; and stretching the protruding portion in a width direction perpendicular to the carrying direction by allowing a part or whole of the wave-shaped edge that is sucked in the inclined slit portion to emerge onto the contact surface of the carrying section from the inclined slit portion as the first sheet material is carried.

2. The carrying method according to claim 1, further comprising the step of performing a predetermined process on the protruding portion being stretched in the width direction.

3. The carrying method according to claim 2, wherein the predetermined process is performed by bonding another object on the protruding portion being stretched.

4. The carrying method according to claim 2, wherein the first sheet material and a second sheet material different from the first sheet material are carried in parallel to each other, and wherein the predetermined process is performed by placing an absorbent body so as to bridge between the first sheet material and the second sheet material at a position of a downstream half of the inclined slit portion in the relative direction and/or a downstream slit portion that is continuous with a downstream end of the inclined slit portion in the relative direction.

5. The carrying method according to claim 1, wherein a force by which the wave-shaped edge is sucked into the inclined slit portion is greater than a force by which the protruding portion is shrunk in the width direction.

* * * * *